(12) United States Patent
Patwardhan

(10) Patent No.: US 11,452,455 B2
(45) Date of Patent: Sep. 27, 2022

(54) SKIN REFLECTANCE AND OILINESS MEASUREMENT

(71) Applicant: Canfield Scientific, Incorporated, Parsippany, NJ (US)

(72) Inventor: Sachin V. Patwardhan, Mount Tabor, NJ (US)

(73) Assignee: Canfield Scientific, Incorporated, Parsippany, NJ (US)

( * ) Notice: Subject to any disclaimer, the term of this patent is extended or adjusted under 35 U.S.C. 154(b) by 0 days.

(21) Appl. No.: 16/402,155

(22) Filed: May 2, 2019

(65) Prior Publication Data

US 2019/0336003 A1 Nov. 7, 2019

Related U.S. Application Data

(60) Provisional application No. 62/666,022, filed on May 2, 2018.

(51) Int. Cl.
*A61B 5/00* (2006.01)
*G06T 7/42* (2017.01)
(Continued)

(52) U.S. Cl.
CPC ............ *A61B 5/0077* (2013.01); *A61B 5/442* (2013.01); *G06K 9/00* (2013.01); *G06T 7/174* (2017.01);
(Continued)

(58) Field of Classification Search
CPC ..... A61B 5/0075; A61B 5/0077; A61B 5/442; A61B 5/443; A61B 5/4848; A61B 5/444; A61B 2576/02; A61B 5/00; A61B 5/1032; A61B 5/441; A61B 5/445; A61B 5/7246; G06K 9/00; G06T 2207/10152; G06T 2207/20064; G06T 2207/20212; G06T 2207/20221; G06T 2207/30088; G06T 2207/30196; G06T 5/50; G06T 7/0012; G06T 7/174; G06T 7/30; G06T 7/42; H04N 5/2256; G01N 21/21; G01N 21/25; G01N 21/57

See application file for complete search history.

(56) References Cited

U.S. PATENT DOCUMENTS

2012/0172685 A1* 7/2012 Gilbert ................... A61B 5/411
600/306
2015/0062380 A1* 3/2015 Nakamura ............ G06T 7/0012
348/234

(Continued)

OTHER PUBLICATIONS

Imaging skin with polarized light S.L. Jacques ; J.C. Ramella-Roman ; K. Lee Proceedings of the Second Joint 24th Annual Conference and the Annual Fall Meeting of the Biomedical Engineering Society] (Year: 2002).*

*Primary Examiner* — Michael J Vanchy, Jr.

(57) ABSTRACT

Apparatuses and methods are disclosed for generating a quantitative indication of the degree of oiliness of skin. In exemplary embodiments, a difference image generated from parallel- and a cross-polarized images of an area of skin is subjected to an intensity thresholding operation. An oiliness metric is generated based on the average intensity of those pixels whose intensities do not exceed the threshold, and/or on the average intensity of those pixels whose intensities exceed the threshold. An indication based on the metric is generated and output.

22 Claims, 6 Drawing Sheets

(51) Int. Cl.
*G06T 7/30* (2017.01)
*G06T 7/174* (2017.01)
*H04N 5/225* (2006.01)
*G06K 9/00* (2022.01)
*G06T 7/00* (2017.01)

(52) U.S. Cl.
CPC ............... *G06T 7/30* (2017.01); *G06T 7/42* (2017.01); *H04N 5/2256* (2013.01); *A61B 5/0075* (2013.01); *A61B 5/443* (2013.01); *G06T 7/0012* (2013.01); *G06T 2207/10152* (2013.01); *G06T 2207/20064* (2013.01); *G06T 2207/20212* (2013.01); *G06T 2207/30088* (2013.01); *G06T 2207/30196* (2013.01)

(56) References Cited

U.S. PATENT DOCUMENTS

| | | | | |
|---|---|---|---|---|
| 2015/0374277 | A1* | 12/2015 | Patwardhan | A61B 5/0013 600/306 |
| 2016/0098614 | A1* | 4/2016 | Yamanashi | H04N 5/2256 348/135 |
| 2018/0184967 | A1* | 7/2018 | Yoshida | A61B 5/0077 |
| 2019/0125249 | A1* | 5/2019 | Rattner | A61B 5/443 |
| 2019/0295728 | A1* | 9/2019 | Jeong | A45D 44/00 |

* cited by examiner

SKIN REFLECTANCE AND OILINESS MEASUREMENT

RELATED APPLICATIONS

This Application claims priority from U.S. Provisional Patent Application No. 62/666,022 filed May 2, 2018 and incorporated herein by reference in its entirety.

BACKGROUND INFORMATION

The present disclosure relates to image processing and analysis, particularly the quantitative characterization of reflectance and oiliness of human skin.

In selecting medical or cosmetic treatments or products to be applied to human skin, it is helpful to assess the condition of the skin, before, during and after such applications. A condition of the skin that is often of interest is the "oiliness" of the skin, which is typically assessed by human observation. Whether made by the subject or even a professional, such an observation-based assessment, however, is largely subjective, difficult to quantify, and prone to wide variability. Additionally, some time and effort is required on the part of the observer to make, communicate, and record their assessment. The aforementioned issues are particularly problematic, for example, in studies where products or treatments are applied to large numbers of subjects and the efficacy thereof is to be assessed.

SUMMARY OF THE DISCLOSURE

The present disclosure sets out a method comprising: obtaining a parallel-polarized image of a skin area; obtaining a cross-polarized image of the skin area; generating a difference image from the parallel and cross-polarized images; determining an oiliness metric using the difference image; and outputting an indication of the oiliness metric.

The present disclosure also sets out an apparatus comprising: a storage device configured to store instructions; and a processor configured to execute instructions stored in the storage device to: obtain a parallel-polarized image of a skin area; obtain a cross-polarized image of the skin area; generate a difference image from the parallel and cross-polarized images; determine an oiliness metric using the difference image; and output an indication of the oiliness metric.

These and other aspects of such apparatuses and methods and exemplary variants thereof are described in greater detail below.

BRIEF DESCRIPTION OF THE DRAWINGS

A more complete understanding of the present disclosure may be realized by reference to the accompanying drawings.

DETAILED DESCRIPTION

Figure 1:
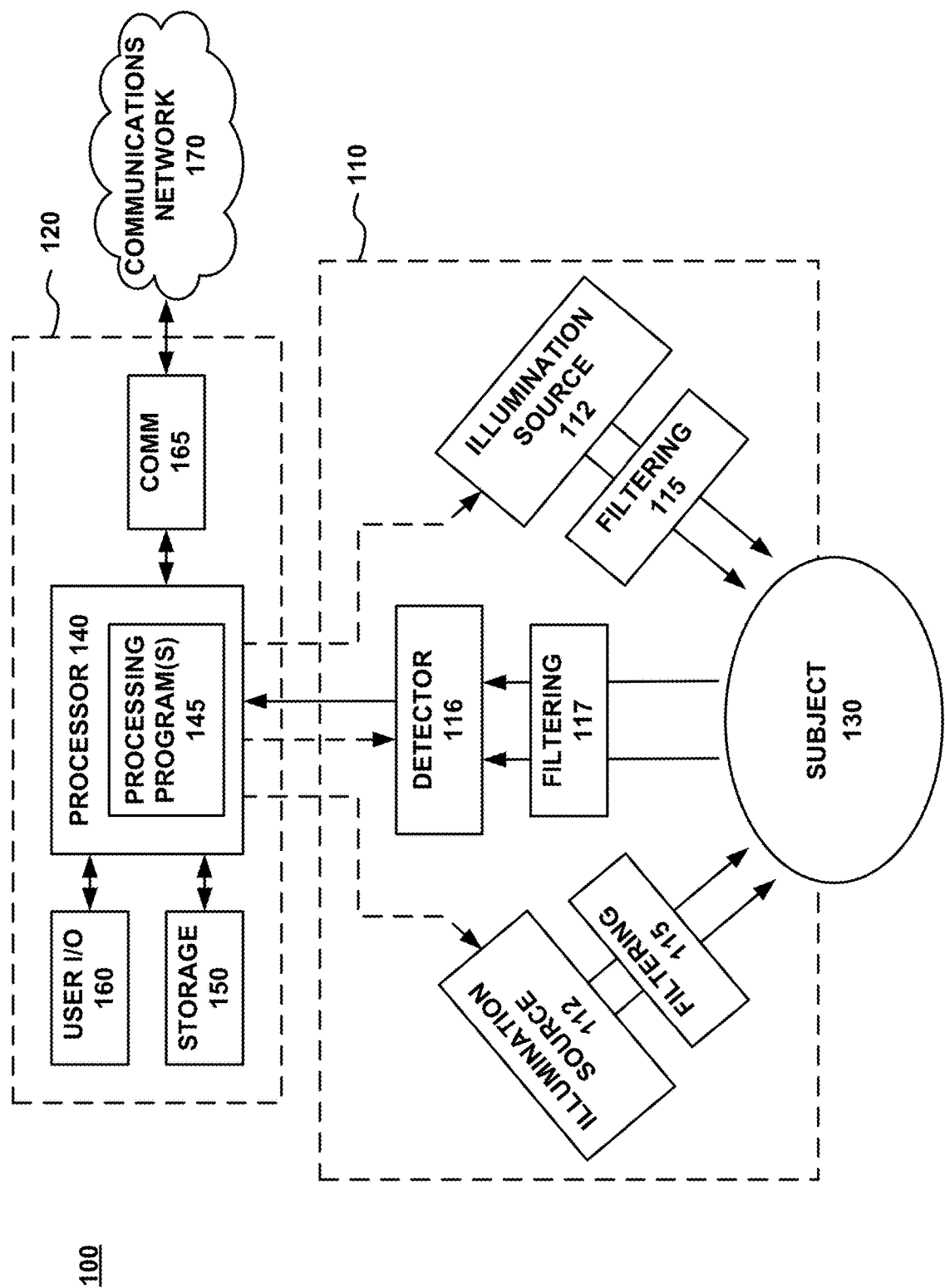
FIG. 1 is a schematic representation of an exemplary system in accordance with the present disclosure.

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In addition, it will be appreciated by those skilled in art that any flow charts, flow diagrams, and the like represent various processes which may be substantially represented in computer readable medium and so executed by a computer or processor, whether or not such computer or processor is explicitly shown.

The functions of the various elements shown in the drawings, including any functional blocks, steps, procedures, modules, units or the like may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, dedicated circuitry, digital signal processor (DSP) hardware, network-based processors, application specific integrated circuitry (ASIC), read-only memory (ROM), random access memory (RAM), and non-volatile storage. Other hardware, conventional and/or custom, may also be included.

Software modules, or simply modules which are implied to be software, may be represented herein as any combination of flow chart elements or other elements indicating performance of process steps and/or textual description.

Such modules may be executed by hardware that is expressly or implicitly shown.

As used herein, the term "image" may encompass any form of photo-documentation, including 2D images and/or 3D surfaces and/or 3D volumetric image data, where a 2D image could be a single or a multichannel visible impression obtained by a camera, a 3D surface could be points in a 3D space connected by line segments to form a polygonal mesh along with any associated 2D images that represent the underlying texture and a 3D volumetric image data might represent a stack of 2D images that represent a 3D volume of the object being imaged, such as a stack of MRI images.

FIG. 1 schematically depicts an exemplary system 100 in accordance with the present disclosure for assessing the oiliness of human skin. As shown in FIG. 1, components of system 100 include an image capture system 110 coupled with a processing system 120. Image capture system 110 may include one or more hand-held or mounted point-and-shoot or DSLR cameras, mobile cameras, frontal or rear-facing smart-device cameras, dermatoscopes (e.g., Canfield Scientific Inc.'s VEOS), 2D skin imaging systems (e.g., Canfield Scientific Inc.'s VISIA, VISIA-CR), 3D human body imaging devices (e.g., Canfield Scientific Inc.'s VECTRA), Canfield Scientific Inc.'s NEXA system, 3D Total Body systems (e.g., Canfield Scientific Inc.'s WB360), and/or 3D volumetric imaging devices, among others.

In exemplary embodiments, image capture system 110 includes one or more illumination sources 112 which are activated to shine light onto a subject's skin 130 through a respective filtering element 115. Light reflected or emitted from the subject tissue 130 is captured by a detector 116 through a filtering element 117. Each filtering element 115, 117 may include one or more filters for passing or blocking light of a selected wavelength or band of wavelengths, and/or polarizers, collectively "filters," which can be selectively placed in or out of the respective optical path of the filtering element. In exemplary embodiments, detector 116 may comprise a camera, such as a conventional digital SLR camera or the like, a digital video camera, or multiple one- or two-dimensional detectors, with similar or different characteristics. Multiple detectors 116 can be arranged to capture two- or three-dimensional images.

Advantageously, the captured images can be single mode or multimodal—including, for example, those from standard white light, polarized light, and/or fluorescent light—captured at selected wavelengths and/or illuminated with selected wavelengths of light. Note that the term "light" as used herein is not necessarily limited to humanly visible electromagnetic radiation, and may include portions of the electromagnetic spectrum outside the visible range.

Images captured by image capture system 110 are provided to processing system 120 for processing as described below. Of further advantage, processing system 120 may also control image capture system 110, for example, by controlling one or more aspects of the image capture and/or illumination of the subject, such as exposure, modality, or filtering, among others.

Images may also be provided to processing system 120 from other sources and by other means. For example, images may be provided via communications network 170, or in a non-transient, computer-readable storage medium, such as storage 150.

Processing system 120 includes a processor 140 that may be coupled to storage 150, for storing and retrieving images, among other data, and to input/output devices 160, such as a display device and/or user input devices, such as a keyboard, mouse, touchscreen, or the like. Processor 140 may also be coupled to a communications module 165 for interconnection with a communications network 170, such as the Internet, for transmitting and receiving images and/or data, and/or receiving commands, software updates or the like. Processing system 120 may be implemented, for example, with one or more central processing units, computers, workstations, PCs, tablet computers or the like, operating in accordance with one or more programs 145 embodied in a compatible, non-transient, computer-readable storage medium. The interface between image capture system 110 and processing system 120 can be wired, wireless, direct, or indirect (e.g., via a network, Internet.)

It should be noted that the exemplary system 100 illustrates just one of a variety of possible arrangements contemplated by the present disclosure. For example, the various elements of system 100 need not be co-located. For example, image capture system 110 and I/O devices 160 can be located in a dermatologist's office and processor 140 and storage 150 can be remotely located, functioning within a tele-dermatology framework, or may be "cloud-based," interacting with image capture system 110 and I/O devices 160 over communications network 170. In other exemplary arrangements, I/O devices 160 can be remotely located from image capture system 110, thereby allowing a user to remotely examine subjects' images.

Figure 2:
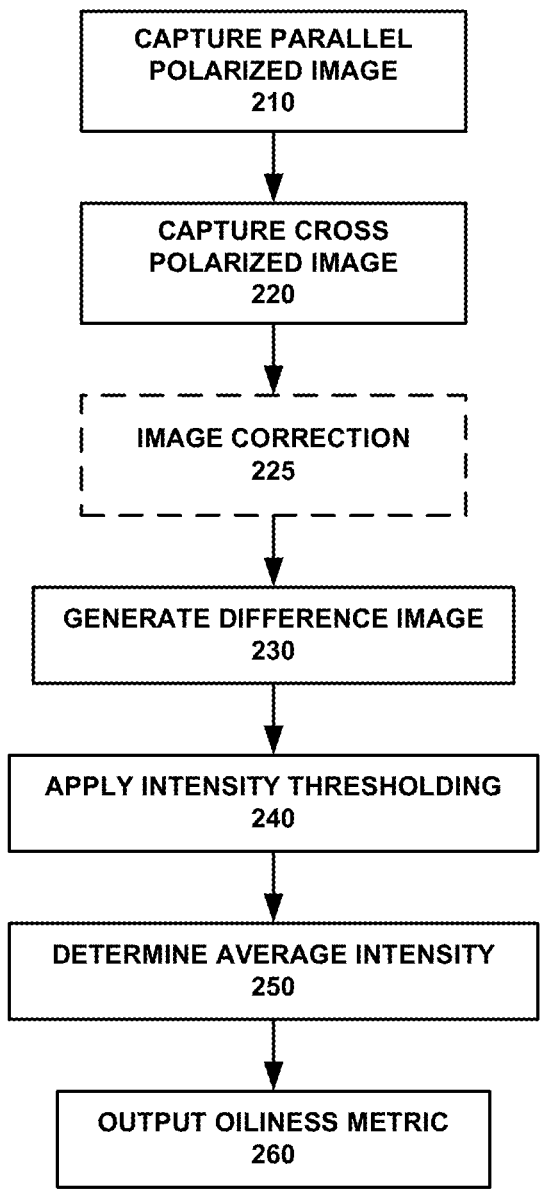
FIG. 2 is a flow chart depicting an exemplary method in accordance with the present disclosure.

FIG. 2 is a flowchart depicting an exemplary process 200, such as would be carried out with exemplary system 100 in accordance with the present disclosure. It is contemplated that in carrying out the exemplary image capture process, the system 100 operates in accordance with program(s) 145 executed by processor 140.

Figure 3A:
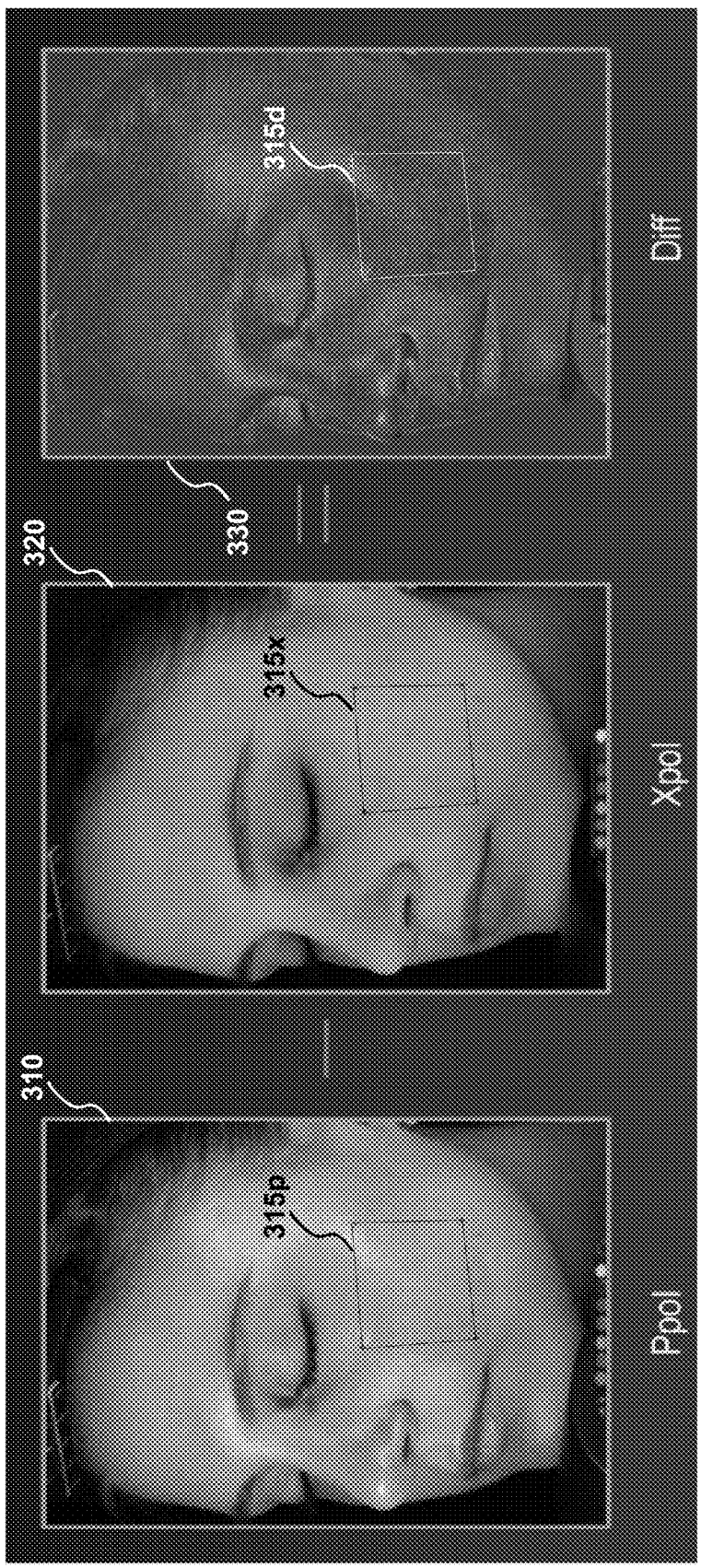
FIGS. 3A and 3B show illustrative images used to describe the exemplary method of FIG. 2.

As shown in FIG. 2, operation begins at 210 with the capture of a parallel-polarized image, such as with image capture system 110. In capturing such an image, the subject 130 is illuminated with light that is linearly polarized with a given orientation and an image of the subject thus illuminated is captured through a linear polarized filter of the same orientation. An illustrative parallel-polarized image (Ppol) 310 is shown in FIG. 3A.

Although broad-spectrum (white light) illumination can be used, because skin surface oiliness is superficial and imaging thereof does not entail looking deep inside the skin, a shorter wavelength spectral-band illumination can also be used in implementations consistent with the present disclosure. Longer wavelength illumination, such as in the red band, which can penetrate to greater skin depths, can be avoided. Additionally, while linear polarization is described, circular polarization can also be used.

Operation then proceeds to 220 in which a cross-polarized image of the subject 130 is captured. In capturing such an image, the subject 130 is illuminated with light that is linearly polarized with a given orientation and an image of the subject thus illuminated is captured through a linear polarized filter of an orientation orthogonal to that of the illuminating light. An illustrative cross-polarized image (Xpol) 320 is shown in FIG. 3A.

As can be appreciated, the order in which the parallel- and cross-polarized images are captured, as represented by blocks 210 and 220, can be reversed. Preferably, the images are captured using flash illumination and in temporal proximity to each other, with the subject stationary so as to avoid or minimize the effects of any movement or changes in the subject's pose. Note that images 310 and 320 are of the same area of the subject's face, with the same pose, and captured from the same angle. Additionally, to maintain consistency between images, the same illumination source(s) are preferably used for both images, with polarization of the illumination provided, for example, using a polarizer that can be rotated to the desired orientation for each image, a filter wheel, or other suitable arrangement allowing illumination of orthogonal polarizations to be selectively emitted from the same point(s). Alternatively, the same illumination polarization can be used for both parallel- and cross-polarized images, and the polarizer in front of the camera rotated or changed.

When capturing the broad-spectrum white light cross- and parallel-polarized images, the imaging device parameters preferably are set so that both images have the same dynamic range. Additionally, care should be taken to set the imaging device parameters to avoid saturated areas or "hot-spots" due to strong reflections (particularly in the parallel-polarized image), which can be mistaken for semi-covered oily skin areas.

After the parallel- and cross-polarized images have been captured, correction such as for light output variations, registration (elastic or non-elastic), color calibration, or other suitable corrective processing (collectively or individually "image correction") of the images 310 and/or 320 can be optionally performed at 225. Whether such processing is performed can depend on how closely the images match each other. For example, if captured in a controlled environment, such as with a VISIA system, correction at 225 should not be necessary. In any case, correction may be performed for best results.

Operation then proceeds to 230 in which a difference image is generated based on the parallel- and cross-polarized images. In exemplary implementations, the difference image is generated by subtracting the intensity of each pixel of the cross-polarized image from the intensity of the corresponding pixel of the parallel-polarized image to determine the intensity of the corresponding pixel of the difference image. The resultant pixel difference values can then be scaled to a range of positive values (such as an 8-bit grayscale, for example). An illustrative difference image (Diff) 330 is shown in FIG. 3A. For a white light illuminated image captured with a conventional color camera (such as the Ppol and Xpol images shown in FIG. 3A), the intensity of an individual pixel of the image can be determined as the mean of the intensities of the red, green and blue components of the pixel.

Alternatively, the difference image can be determined based on a subset of the color components of the parallel- and cross-polarized images, such as the green or blue color components. It should be noted that as long as the illumination used in capturing the cross- and parallel-polarized image is the same, it should not matter which color or wavelength is used for generating the differential measurement. However, longer-wavelength components of the illumination such as red, penetrate deeper into the skin and will have less diffuse reflectance compared to the shorter-wavelength components. If such longer-wavelength components are used to generate the difference image, it may be necessary to first adjust the relative weights of the parallel- and cross-polarized image components in determining the difference therebetween.

In other implementations, the captured parallel- and cross-polarized images can be transformed to another color space, such as the Lab or L*a*b* color space, and the difference image can be generated based on the difference between the L or L* components of the captured images.

After the difference image has been generated at 230, operation then proceeds to 240 in which an intensity thresholding operation is applied to the difference image. In this operation, pixels of the difference image whose intensities exceed a threshold value are selected for inclusion in a first subset of pixels. Such pixels are graphically depicted in FIG. 3B in red for an area 315$d$ of a portion of the difference image 330 shown in FIG. 3A. Area 315$d$ corresponds to areas 315$p$ and 315$x$ shown respectively in the parallel- and cross-polarized images 310, 320 of FIG. 3A. The gray pixels in the area 315$d$ shown in FIG. 3B represent those pixels whose intensities do not exceed the intensity threshold value.

In an exemplary implementation, the aforementioned intensity threshold value is computed as the 80-95th percentile intensity value from a histogram of the difference image 330. The percentile value can be adjusted depending on the desired detection sensitivity. Alternatively, the intensity threshold value can be computed as the mean intensity value of the difference image plus some multiple of the standard deviation of the intensity, where the multiple is a tunable system-dependent parameter that controls detection sensitivity. The intensity threshold value can be determined in a calibration procedure, as described below.

Figure 3B:
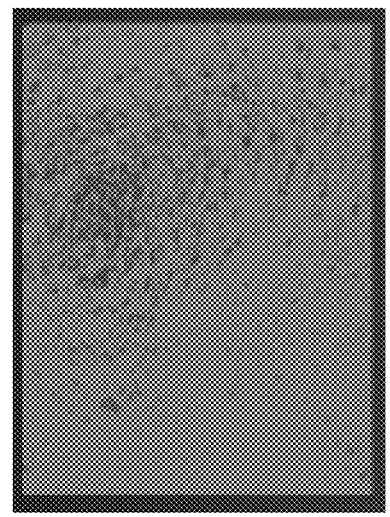

Operation then proceeds to 250 in which the average intensity of the "gray" pixels—those pixels in the difference image whose intensities do not exceed the threshold value applied in the thresholding operation of 240, as exemplified by the pixels shown in gray in FIG. 3B—is determined. As described in greater detail below, the average intensity thus determined, is indicative of the degree of oiliness of the skin area imaged.

In alternative implementations, instead of determining the average intensities of the "gray" pixels in the difference image 330, the average intensities of the pixels in the parallel-polarized image 310 and/or the cross-polarized image 320 corresponding to the aforementioned "gray" pixels in the difference image, can be determined. While the detection of shiny ("red") and background ("gray") areas is still performed using the difference image 330, the intensity values of the corresponding pixels of the parallel- or cross-polarized images 310 or 320 are used to determine the average intensity at 250. In any case, however, detecting the shiny ("red") and background ("gray") areas using the difference image 330, as opposed to the other images 310, 320, is advantageous because it is less susceptible to the influence of source reflections from the air/oil interface. Furthermore, while determining the average intensities of the pixels in the parallel-polarized image 310 or cross-polarized image 320 are possible alternatives, measurements based on the difference image 330 tend to yield more reliable results that are less system- and subject-dependent than results based just on the parallel-polarized image, for example. Even with no oil on the skin, parallel-polarized images will tend to have hot-spots, which are primarily due to source reflection and are dependent on system geometry, and skin features such as curvature and texture. Such hot-spots are where shine is most evident, which is highly susceptible to variability depending on the application of oil.

At 260, an oiliness metric is output based on the average intensity determined at 250. The oiliness metric can be the average intensity value as determined, some proportion thereof, or other suitable metric based thereon. The oiliness metric can be represented in any of a variety of suitable alphanumeric or graphical formats, and can be displayed, stored, processed, or communicated by system 100. An oiliness metric thus obtained can be used in a variety of applications, including clinical, aesthetic, and/or cosmetic studies.

Figure 4A:
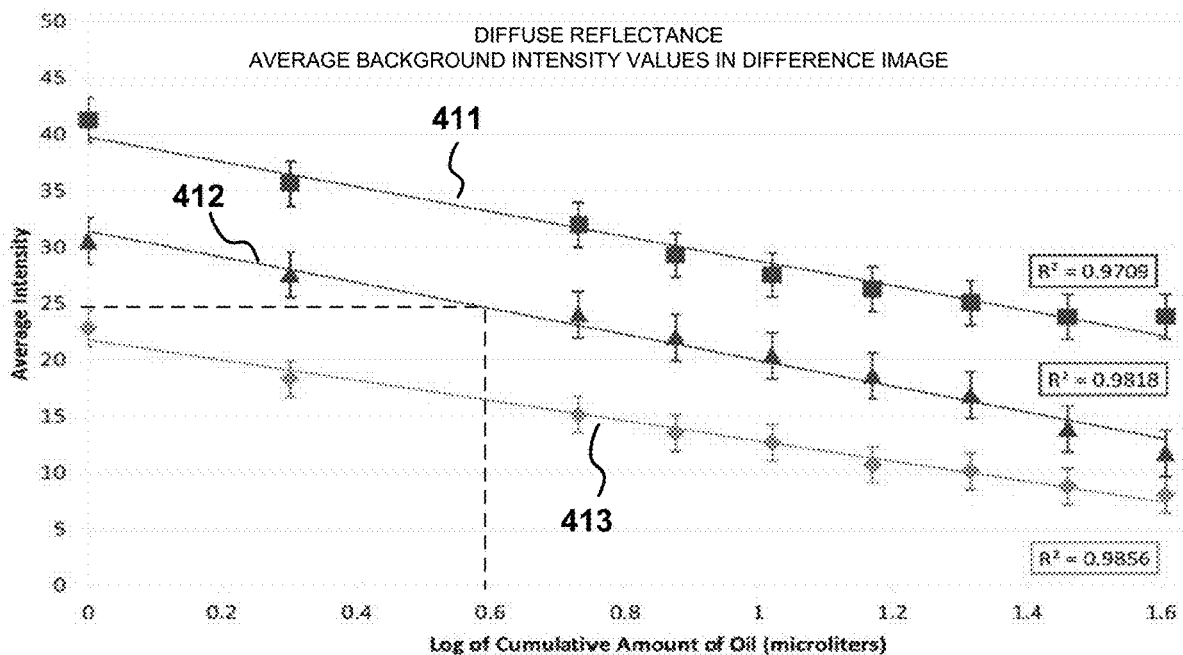
FIGS. 4A and 4B show graphs of results obtained with the method of FIG. 2 carried out using different imaging systems.
Figure 4B:
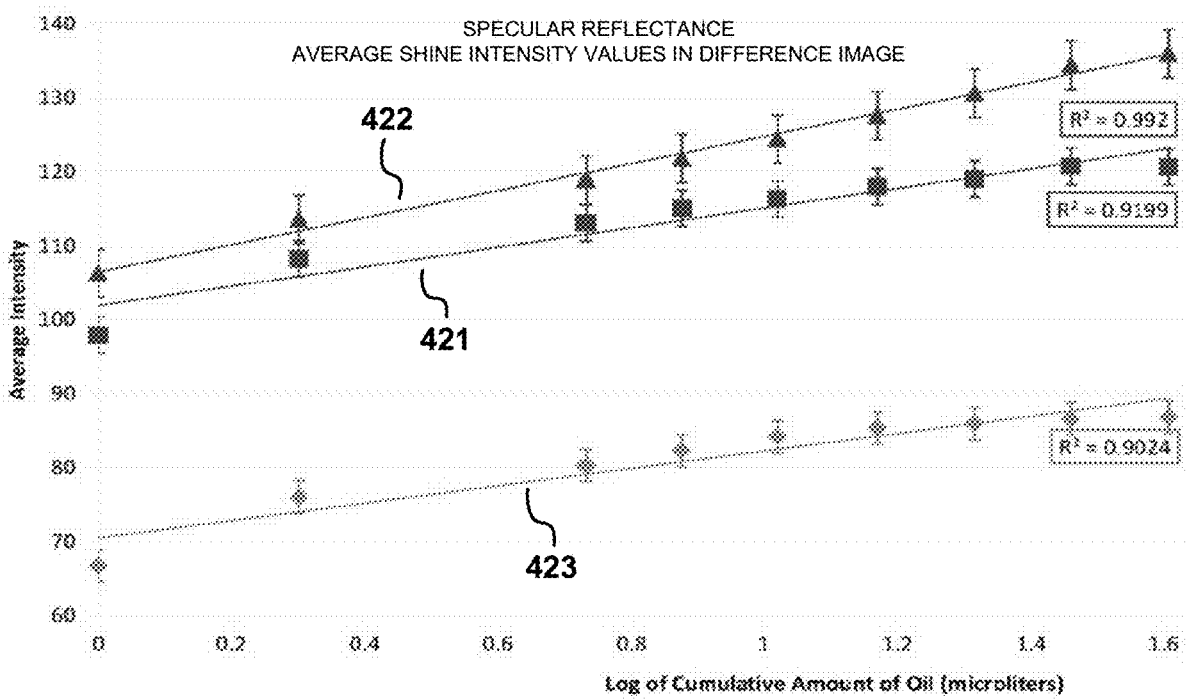

Reference is now made to FIGS. 4A and 4B to further explain the significance of a metric as provided at 260.

FIGS. 4A and 4B represent the results of testing exemplary implementations in accordance with the present disclosure by controllably adding oil incrementally to an area of skin, capturing parallel- and cross-polarized images thereof after each incremental addition of oil, and processing the captured images as described above with respect to method 200.

FIG. 4A shows the relationship between the average intensity such as determined at 250 of those pixels in the difference image whose intensities do not exceed the threshold value applied in the thresholding operation of 240—as exemplified by the pixels shown in gray in FIG. 3B—and the cumulative amount of oil added to an area of skin for which the method 200 has been applied. Lines 411, 412 and 413 represent linear regression results based on measurements taken of multiple subjects using three different imaging systems. As shown in FIG. 4A, the inverse relationship between the amount of oil added and the average intensity of the "gray" pixels, as determined at 250, is clear for all three systems, demonstrating that a metric determined with the method 200 can provide a reliable quantitative representation of skin oiliness.

FIG. 4B shows the relationship between the average intensity of those pixels in the difference image whose intensities exceed the threshold value applied in the thresholding operation of 240—as exemplified by the pixels shown in red in FIG. 3B—and the cumulative amount of oil added to an area of skin for which the method 200 has been applied. Lines 421, 422 and 423 represent linear regression results based on measurements taken with the same imaging systems for which results are shown in FIG. 4A. The increase in average intensity of the "red" pixels with increasing oil is consistent with the decrease in average intensity of the "gray" pixels with oiliness. As oil is added, skin features such as pores, fine lines and wrinkles start submerging in oil, and the skin area above the oil level, or raised features with some oil on them—i.e., the area of specular reflection—decreases. With no or little surface oil, the specular reflection tends to be diffused (i.e., multi-directional), depending on the skin texture and topography. However, as skin features such as pores, fine-lines, and wrinkles start submerging in oil, the specular reflection becomes more directional, hence yielding an increase in mean shine intensity. As such, in addition to or as an alternative to the average intensity of the "gray" pixels, the average intensity of the "red" pixels can also be used in generating an oiliness metric.

As mentioned, the skin areas represented by the "red" pixels are those in which the skin generally has not been submerged in oil and an air/skin interface is predominantly imaged. The "red" pixels may also represent those areas with raised features that have not created a void in the oil layer and thus may have some oil on them. In the areas represented by the "gray" pixels, the skin is generally submerged in oil and an air/oil interface is predominantly imaged. The surface of the oil is smooth, as opposed to the skin, which has texture and curvature. As such, a metric based on the average intensity of the "red" pixels (FIG. 4B), as opposed to a metric based on the average intensity of the "gray" pixels (FIG. 4A), may be noisier due to the skin's texture and curvature. Furthermore, as mentioned, the "red" areas generally represent an air/skin interface and may also include some portions with an oil/skin interface, from which there are surface or specular reflections. In the "gray" areas, there is little or no air/skin interface but rather an air/oil interface and an oil/skin interface beneath that. Under uniform illumination, because the surface of the layer of oil is smoother than skin, surface reflections from the air/oil interface will be more uniform than those from the air/skin interface. No significant surface reflection is expected from the oil/skin interface since the refractive indices of oil and skin are almost the same.

It bears noting that the data from which the graphs in FIGS. 4A and 4B have been generated were collected in a controlled setting, under controlled conditions using a controlled procedure intended to simulate varying levels of naturally occurring skin surface oil by adding known amounts of oil and spreading it over an area of interest. As described above, the area of interest is then divided into two regions (shiny and glossy) based on pixel intensities and the average intensities of those regions are computed. This method provides a reliable metric that tracks well with such simulated conditions. The results obtained and presented in FIGS. 4A and 4B, indicate, therefore, that changes in skin surface oiliness can be reliably measured with method 200 using images captured at two or more time points, such as a first pair of parallel- and cross-polarized images captured in temporal proximity to each other before treatment and a second pair of parallel- and cross-polarized images captured in temporal proximity to each other after treatment, or before and after an interval of time during which a change in the condition of the skin may occur.

Figure 5:
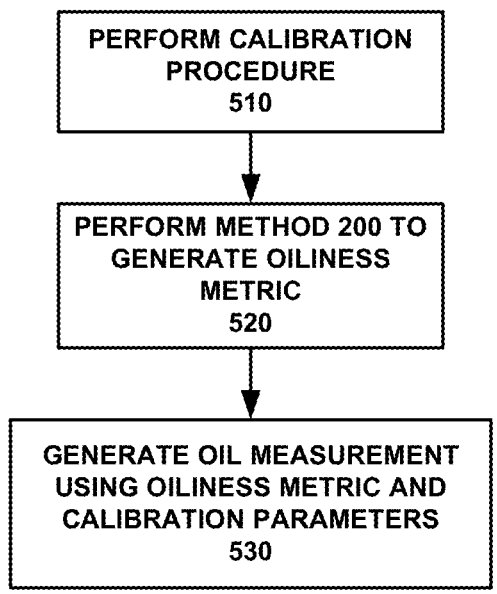
FIG. 5 is a flow chart depicting an exemplary skin oiliness measurement method in accordance with the present disclosure.

Referring now to FIG. 5, an exemplary method 500 in accordance with the present disclosure to provide a measurement of the amount of surface oil at a single time point (i.e., using one set of parallel- and cross-polarized images of the subject captured in temporal proximity to each other) is presented. As shown in FIG. 5, method 500 includes performing at 510 a calibration procedure to generate data and calibration parameters, such as the data and regression analysis information represented by the graph(s) in FIGS. 4A and/or 4B, and/or parameters used in thresholding operation 240. An exemplary implementation of a calibration procedure is described below with reference to FIG. 6.

Using the same system with which the calibration procedure was performed, method 200 is then performed at 520 using a set of parallel- and cross-polarized images captured at the same time point. The oiliness metric generated therefrom is then translated at 530 into a measurement of the amount of surface oil using the results of the calibration procedure, similar to the information represented by the graph(s) of FIGS. 4A and/or 4B. Thus for example, if the calibration procedure at 510 yielded calibration parameters similar to those represented by line 412 in the graph of FIG. 4A, and the performance of method 200 at 530 yielded a "gray" pixel average intensity of 25, the log of the estimated surface oil quantity for the analyzed skin area would be approximately 0.6 (or approximately 4 μL), as indicated by the dashed lines.

Figure 6:
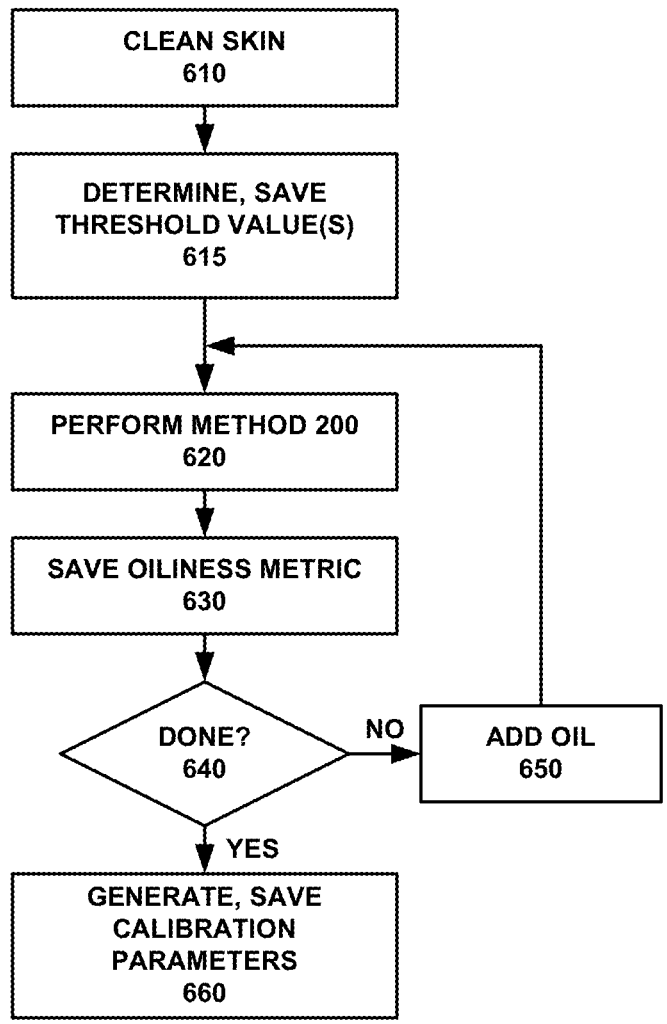
FIG. 6 is a flow chart depicting an exemplary calibration procedure for use in a skin oiliness measurement method or system in accordance with the present disclosure.

With reference now to FIG. 6, an exemplary calibration procedure 600 will now be described. Procedure 600 starts at 610 with cleaning the area of skin to which oil is to be applied and imaged, such as area 315 shown in FIG. 3A.

Operation then proceeds to 615 to determine parameters for the intensity thresholding operation, such as performed at 240 of method 200 to determine shiny ("red") and background ("gray") areas in the difference image (315d). With the subject's skin presumably free of surface oil after cleaning at 610, a pair of parallel- and cross-polarized images are captured, corrected (as needed), and a difference image generated therefrom, as described above for 210-230 of method 200. The minimum, maximum and average intensities of the difference image are then determined and saved. To avoid isolated pixel noise, the minimum and maximum values can be determined, for example, as the $5^{th}$ and 95$^{th}$ percentile values of the difference image pixel intensities. The minimum, maximum, and average intensities thus determined and saved, can be used in the processing of follow-up images of the subject's skin area captured with the same system under similar conditions. More specifically, the average value can be used to determine the threshold value for intensity thresholding operation 240, as described above. Alternatively, the "gray" pixels of a follow-up difference image can be determined to be those pixels whose intensities are less than the minimum intensity of the calibration difference image, and the "red" pixels can be determined to be those whose intensities exceed the maximum intensity of the calibration difference image.

Operation then proceeds to 620, in which method 200, as described above, is performed to generate an oiliness metric for the area of skin. The oiliness metric thus generated is saved at 630 for further processing.

Operation then proceeds to 640 to determine whether the calibration procedure has been completed. If not, operation proceeds to 650 in which an incremental quantity of oil (e.g., 1.0 µL) is added and spread over the area of skin, similarly to the above described testing procedure. As can be appreciated, the incremental and total cumulative amounts of oil will depend on the size of the calibration skin area, which can be for example, a 2"×2" square, or other suitable shape and size.

Once oil has been added at 650, operation returns to 620 to carry out method 200 to image the calibration skin area and to generate a new oiliness metric for the area with the added oil. As before, the newly generated metric is saved at 630, and until it is determined at 640 that sufficient data has been collected for calibration and/or the calibration procedure is otherwise finished, the sequence of incrementally adding oil at 650, performing method 200, and saving the oiliness metric generated thereby, is repeated. In exemplary implementations, method 200 is performed 10 to 20 times, to generate and save a corresponding number of oiliness metric data points.

Once it is determined at 640 that the collection of calibration data is complete, operation proceeds to 660 in which the calibration data saved at 630 are processed and used to generate calibration parameters for the system used in calibration procedure 600. In an exemplary implementation, a regression analysis is performed on the collected data, similarly to that represented graphically in FIGS. 4A and 4B.

Calibration procedure 600 can be carried out once for each subject and the calibration parameters saved in association with the subject. When the subject's skin is analyzed again with the same system, the calibration parameters saved for the subject can be retrieved and used as described above to provide a measure of skin surface oiliness, such as by repeating 520 and 530 of method 500.

Figure 7:
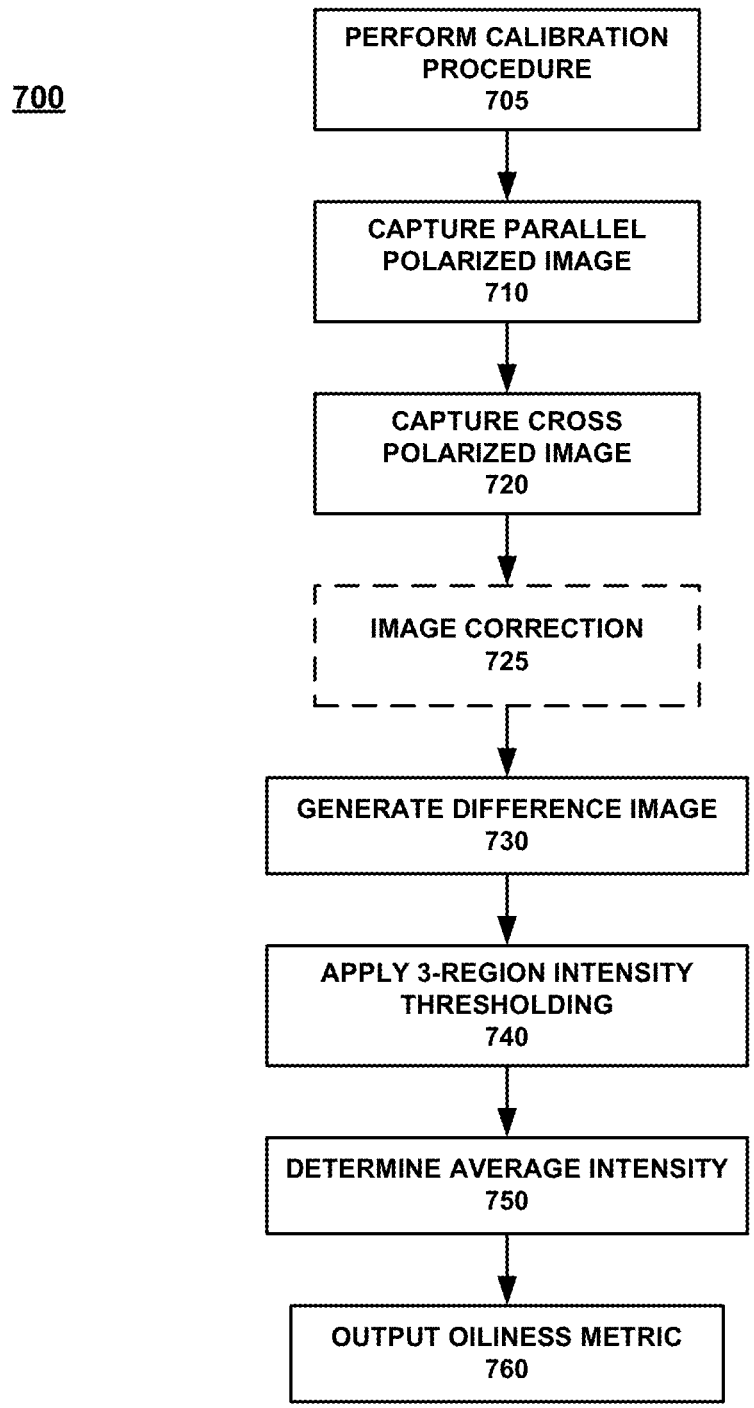
FIG. 7 is a flow chart depicting a further exemplary skin oiliness measurement method in accordance with the present disclosure.

A further exemplary method in accordance with the present disclosure will now be described with reference to FIG. 7, which shows a flowchart of a method 700 which begins at 705 with the performance of calibration procedure 600. As with method 200, operation proceeds with the calibrated system to: capture a parallel-polarized image at 710; capture a cross-polarized image at 720; perform image correction, as needed, at 725; and generate a difference image from the parallel- and cross-polarized images at 730.

Operation then proceeds to 740 in which an intensity thresholding operation is performed on the difference image generated at 730. Unlike the thresholding operation 240 of method 200 in which the difference image is divided into two regions—one representing skin submerged in oil and the other representing skin not submerged or partially submerged in oil due to raised skin features—thresholding operation 740 divides the difference image into three regions: no surface oil, partially submerged in oil, and completely submerged in oil.

In generating data such as that represented in FIGS. 4A and 4B and as described above with respect to calibration procedure 600, the first pair of images are taken after the testing or calibration skin area has been cleaned, and thus ostensibly free of any significant amount of surface oil. With the intensity thresholding operation 240 of method 200, however, the "gray" pixels are treated as representing skin submerged in oil, even in the case of the first pair of images in which there is no significant surface oil. With intensity thresholding operation 740, however, such pixels are classified under a third category representative of skin with no surface oil.

It bears noting that while there will be areas of the imaged skin that do not have significant surface oil in the controlled conditions of the above described testing and calibration procedures, this will also be true in real life. For instance, parts of the subject's skin within the imaged area can be oily due to sebum produced by the sebaceous glands of some of the pores within the imaged area. In other parts of the imaged area, however, there may be no sebum production, sebum may not have come to the surface because the pores are clogged, or the subject has partially wiped their face.

Consider a calibrated system characterized by the line 413 in the graph of FIG. 4A showing the average intensity of the background ("gray") pixels in the difference image (315d) as a function of surface oil. As shown in FIG. 4A, an average intensity of "gray" pixels greater than approximately 22 corresponds to 0 µL of surface oil. Therefore, after detecting and separating the shiny areas (as represented by the "red" pixels in FIG. 3B), operation 740 further sub-divides the remaining region into a gray sub-region (in which surface oil is present, as represented by those pixels of the difference image with intensities less than approximately 22 corresponding to the 0 surface oil level) and a third ("blue") sub-region in which there is no surface oil, as represented by those otherwise "gray" pixels of the difference image with intensities greater than approximately 22.

The thresholds used in thresholding operation 740 can also be obtained from calibration procedure 600. As described above, the background ("gray") pixels of the difference image can be determined to be those pixels whose intensities are less than the minimum intensity threshold value determined at 615, whereas the shiny ("red") pixels can be determined to be those whose intensities exceed the maximum intensity threshold value determined at 615. The remaining pixels can be deemed to be the "blue" pixels, representing the oil-free sub-region.

After thresholding operation 740, operation proceeds to 750 in which the average intensity of the "red" or "gray" pixels as determined at 740 is computed, similarly to 250 in method 200. In the case of method 700, however, the "gray" pixels do not include the oil-free ("blue") pixels, as those have been separated out in operation 740, and thus their intensities are not included in the determination of the average intensity at 750.

Additional testing of exemplary implementations in accordance with the present disclosure demonstrate a strong correlation with averages of Investigators Global Assessment (IGA) scores obtained from physician assessments. Accordingly, in further exemplary implementations, apparatuses and methods are provided for generating a set of images (e.g., five) that are photo-numerically indexed (and can be based on skin type) that a user (e.g., MD) can use to grade a subject by visual comparison to the images.

It bears noting that skin oiliness measurement depends in part on skin texture. Rough skin will require more oil to be completely submerged as compared to smooth skin. Accordingly, the accuracy of an oiliness metric obtained as described above can be improved by taking skin texture into account, so that the oiliness metric is greater for rougher skin and lower for smoother skin, all else being equal. For this purpose, a method for assessing skin texture that can be used in exemplary implementations is described in U.S. patent application Ser. No. 16/402,149, filed May 2, 2019, entitled SKIN ASSESSMENT USING IMAGE FUSION, incorporated herein by reference in its entirety. In exemplary implementations, a skin texture roughness metric generated in accordance with that disclosure can be used to adjust the oiliness metric generated in accordance with the present disclosure.

Employing such a technique, a skin texture metric can be obtained, which can be combined with the oiliness metric obtained as described above to derive a texture-compensated oiliness metric that more accurately indicates the quantity of oil in the analyzed area of skin. In exemplary implementations, the oiliness metric obtained by the above-described method can be adjusted using a correction based on skin texture so as to yield an increased oiliness metric with increased skin roughness, and vice versa.

While the above-described method is independent of skin darkness, because currently accepted oiliness assessment methodologies are based on human observation and because shiny areas appear more easily visible on darker skin, it may be preferable that the oiliness metric be dependent on skin darkness so as to more closely align results in accordance with the present disclosure to those expected with current, observation-based methodologies. In exemplary implementations, as in the case of skin roughness described above, the oiliness metric obtained by the above-described method can be adjusted using a correction based on skin darkness so as to yield an increased oiliness metric with increased skin darkness, and vice versa.

One or more of the metrics generated as described herein can be used to generate a photo-numeric scale for visual grading of skin oiliness.

In addition to measuring and evaluating treatment efficacy using before and after images and/or measurements, as described, implementations in accordance with the present disclosure can also be used in measurement-based treatment and/or making treatment suggestions, among other applications.

The foregoing merely illustrates principles of the present disclosure and it will thus be appreciated that those skilled in the art will be able to devise numerous alternative arrangements which, although not explicitly described herein, embody the principles of the present disclosure and are within its spirit and scope. For instance, as can be appreciated, a variety of arrangements of cameras and light sources are contemplated consistent with the present disclosure. In addition, while embodiments using white light illumination have been described, embodiments in accordance with the present disclosure may also be adapted for illumination of any suitable band or bands of wavelengths. Additionally, although illustrated as single elements, each such block or step shown may be implemented with multiple blocks or steps, or various combinations thereof. Also terms such as "software," "application," "program," "firmware," or the like, are intended to refer, without limitation, to any instruction or set of instructions, structure, or logic embodied in any suitable machine-readable medium. It is to be understood that numerous modifications may be made to the illustrative embodiments and that other arrangements may be devised without departing from the spirit and scope of the present invention as defined by the appended claims.

What is claimed is:

1. A method comprising:
   obtaining a parallel-polarized image of a skin area;
   obtaining a cross-polarized image of the skin area;
   generating a difference image from the parallel and cross-polarized images;
   determining at least one portion of the difference image representative of a corresponding at least one portion of the skin area exhibiting uniform reflectance, wherein the at least one portion of the skin area exhibiting uniform reflectance corresponds to at least one portion of the difference image having an intensity less than a threshold intensity;
   determining an oiliness metric based on the at least one portion of the skin area exhibiting uniform reflectance as having skin surface oil, the oiliness metric being indicative of a skin surface oil quantity, including determining an average intensity of pixels of the difference image having intensities less than the threshold intensity; and
   outputting an indication of the oiliness metric.

2. The method of claim 1, wherein
   determining the oiliness metric includes determining at least one of: an average intensity of pixels of the parallel-polarized image corresponding to said pixels of the difference image having intensities less than the threshold intensity, or an average intensity of pixels of the cross-polarized image corresponding to said pixels of the difference image.

3. The method of claim 1 comprising:
   illuminating the skin area with polarized light of a first polarization orientation;
   capturing the parallel-polarized image with polarized filtering of the first polarization orientation; and
   capturing the cross-polarized image with polarized filtering of a second polarization orientation, wherein the first and second polarization orientations are mutually orthogonal.

4. The method of claim 1, wherein determining the oiliness metric includes determining the oiliness metric in accordance with at least one of a skin color or a skin texture.

5. The method of claim 1 comprising performing one or more correction operations on at least one of the parallel-polarized image or the cross-polarized image of the skin area.

6. The method of claim 1 comprising performing a calibration operation.

7. The method of claim 1, wherein the intensity threshold is determined in accordance with an 80-95th percentile intensity value of the difference image.

8. The method of claim 1, wherein the threshold intensity is set so as to exclude from the at least one portion of the difference image any part of the skin area without surface oil.

9. The method of claim 1 comprising determining the skin surface oil quantity using the oiliness metric.

10. A non-transient computer readable storage medium containing instructions for execution by a processor for carrying out the method of claim 1.

11. An apparatus comprising:
    a storage device configured to store instructions; and a processor configured to execute instructions stored in the storage device to:
  obtain a parallel-polarized image of a skin area;
  obtain a cross-polarized image of the skin area;
  generate a difference image from the parallel and cross-polarized images;
  determine at least one portion of the difference image representative of a corresponding at least one portion of the skin area exhibiting uniform reflectance wherein the at least one portion of the skin area exhibiting uniform reflectance corresponds to at least one portion of the difference image having an intensity less than a threshold intensity;
  determine an oiliness metric based on the at least one portion of the skin area exhibiting uniform reflectance as having skin surface oil, the oiliness metric being indicative of a skin surface oil quantity, including determining an average intensity of pixels of the difference image having intensities less than the threshold intensity; and
  output an indication of the oiliness metric.

12. The apparatus of claim 11, wherein determining the oiliness metric includes determining at least one of: an average intensity of pixels of the parallel-polarized image corresponding to said pixels of the difference image having intensities less than the threshold intensity, or an average intensity of pixels of the cross-polarized image corresponding to said pixels of the difference image.

13. The apparatus of claim 11 comprising:
an illumination source, wherein the illumination source is configured to illuminate the skin area with polarized light of a first polarization orientation; and
an image capture device with polarized filtering of a second polarization orientation,
wherein at least one of the first and second polarization orientations is selectable so that the polarization orientations are the same for capturing the parallel-polarized image of the skin area and mutually orthogonal for capturing the cross-polarized image of the skin area.

14. The apparatus of claim 11, wherein determining the oiliness metric includes determining the oiliness metric in accordance with at least one of a skin color or a skin texture.

15. The apparatus of claim 11, wherein the processor is configured to execute instructions to perform one or more correction operations on at least one of the parallel-polarized image or the cross-polarized image of the skin area.

16. The apparatus of claim 11, wherein the processor is configured to execute instructions to perform a calibration operation.

17. The apparatus of claim 11, wherein the intensity threshold is determined in accordance with an 80-95th percentile intensity value of the difference image.

18. The apparatus of claim 11, wherein the threshold intensity is set so as to exclude from the at least one portion of the difference image any part of the skin area without surface oil.

19. The apparatus of claim 11, wherein the processor is configured to execute instructions to determine the skin surface oil quantity using the oiliness metric.

20. The apparatus of claim 11, wherein the processor is configured to execute instructions to generate at least one of a treatment evaluation or a treatment suggestion.

21. A method comprising:
  obtaining a parallel-polarized image of a skin area;
  obtaining a cross-polarized image of the skin area;
  generating a difference image from the parallel and cross-polarized images;
  determining at least one portion of the difference image representative of a corresponding at least one portion of the skin area exhibiting specular reflectance, including determining at least one portion of the difference image having an intensity greater than a threshold intensity;
  determining at least one portion of the difference image representative of a corresponding at least one portion of the skin area exhibiting uniform reflectance, including determining at least one portion of the difference image having an intensity less than the threshold intensity;
  determining an oiliness metric based on the at least one portion of the skin area exhibiting uniform reflectance as having skin surface oil, the oiliness metric being indicative of a skin surface oil quantity, including determining: (i) an average intensity of said pixels of the difference image having intensities greater than the threshold intensity, and (ii) an average intensity of pixels of the difference image having intensities less than the threshold intensity; and
  outputting an indication of the oiliness metric.

22. An apparatus comprising:
a storage device configured to store instructions; and
a processor configured to execute instructions stored in the storage device to:
  obtain a parallel-polarized image of a skin area;
  obtain a cross-polarized image of the skin area;
  generate a difference image from the parallel and cross-polarized images;
  determine at least one portion of the difference image representative of a corresponding at least one portion of the skin area exhibiting specular reflectance, including determining at least one portion of the difference image having an intensity greater than a threshold intensity;
  determine at least one portion of the difference image representative of a corresponding at least one portion of the skin area exhibiting uniform reflectance including determining at least one portion of the difference image having an intensity less than the threshold intensity;
  determine an oiliness metric based on the at least one portion of the skin area exhibiting uniform reflectance as having skin surface oil, the oiliness metric being indicative of a skin surface oil quantity, including determining: (i) an average intensity of said pixels of the difference image having intensities greater than the threshold intensity, and (ii) an average intensity of pixels of the difference image having intensities less than the threshold intensity; and
  output an indication of the oiliness metric.

* * * * *